United States Patent [19]
Haydel, Jr.

[11] Patent Number: 6,149,631
[45] Date of Patent: Nov. 21, 2000

[54] DRIP IMPINGING INTRAVENOUS DRIP CHAMBER

[76] Inventor: Leo Joseph Haydel, Jr., 350 Broadway St., New Orleans, La. 70118

[21] Appl. No.: 09/393,894

[22] Filed: Sep. 10, 1999

[51] Int. Cl.[7] ..................................................... A61M 5/00
[52] U.S. Cl. .................................. 604/251; 128/DIG. 13; 604/255
[58] Field of Search ..................................... 604/251–255, 604/246, 403, 405–407, 122, 126, 80–81; 128/DIG. 13

[56] References Cited

U.S. PATENT DOCUMENTS

| | | |
|---|---|---|
| 4,013,072 | 3/1977 | Jess . |
| 4,175,558 | 11/1979 | Hess, III et al. . |
| 4,227,525 | 10/1980 | Lundquist . |
| 4,317,473 | 3/1982 | Gaydos . |
| 4,395,260 | 7/1983 | Todd et al. . |
| 4,504,263 | 3/1985 | Steuer et al. . |
| 4,601,712 | 7/1986 | Cole et al. . |
| 4,781,698 | 11/1988 | Parren . |
| 5,102,400 | 4/1992 | Leibinsohn . |
| 5,364,371 | 11/1994 | Kamen . |
| 5,575,779 | 11/1996 | Barry . |
| 5,776,109 | 7/1998 | Urrutia . |

*Primary Examiner*—Sharon Kennedy
*Assistant Examiner*—LoAn H. Thanh
*Attorney, Agent, or Firm*—Jones, Walker, Waechter, Poitevent, Carrere & Denegre, L.L.P.

[57] ABSTRACT

A drip chamber including an inlet member, a transparent housing chamber and an outlet member wherein an impinging member connected to the inlet member breaks the flow of the intravenous fluid when the fluid forms a indiscernible fluid stream to cause the fluid to accumulate into droplets that are readily visible by medical personnel.

4 Claims, 2 Drawing Sheets

DRIP IMPINGING INTRAVENOUS DRIP CHAMBER

BACKGROUND OF THE INVENTION

1. Field of the Invention

The present invention relates to an improved drip chamber for use with intravenous fluid administration sets, and more particularly, to a drip chamber that includes an impinging member positioned in the flow path of the fluid such that the fluid strikes the impinging member and accumulates into droplets that are visible to medical personnel through the sidewalls of the drip chamber.

2. General Background

The use of drip chambers by medical personnel to regulate the flow of intravenous fluids to a patient are well known in the art. Generally, the drip chambers of such prior art devices are transparent to allow medical personnel to observe the flow rate or "drip" of the fluid and regulate the rate of delivery of the fluid to the patient. Illustrative prior art devices are described in U.S. Pat. No. 5,776,109, issued Jul. 7, 1998, to Hector Urrutia for a "Drip Chamber for Intravenous Fluid Delivery System", U.S. Pat. No. 4,601,712, issued Nov. 16, 1983, to James E. Cole et al., for a "Drip Chamber" and U.S. Pat. No. 4,395,260, issued Jun. 1, 1981, to Robert J. Todd et al. for a "Drip Chamber". One of the stated objects of these prior art devices is to introduce apparatus into the drip chamber to prevent the introduction of air bubbles in the pool of fluid contained at the bottom of the drip chamber when the flow rate of the fluid increases and forms a high velocity stream.

By introducing various types of apparatus into the drip chamber, these prior art devices appear to address the problem of air bubbles being introduced into the fluid. However, these devices require the introduction of features into the drip chamber that complicate the design of the drip chamber and may significantly increase manufacturing costs. More importantly, these devices fail to address the problem of the flow rate or "drip" of the fluid no longer being readily visible to medical personnel once the fluid forms a high velocity stream. The difficulty in discerning the high velocity fluid stream is particularly problematic with the use of "mini-drip" intravenous fluid administration sets (i.e. 60 drops/cc). In many lighting conditions, a fluid stream in such sets having a diameter of less than 1 mm will typically be virtually invisible to medical personnel.

The prior art devices that prevent the formation of air bubbles in the fluid pool by diverting the fluid stream against the sidewall of the drip chamber result in the fluid stream flowing down the sidewall and forming a "sheet" of fluid. Although this fluid stream is of a reduced velocity and may no longer form air bubbles in the fluid pool, the fluid stream may still be invisible to medical personnel. Thus, the flow rate of the fluid cannot be easily calculated by the medical personnel.

This same result may occur if the apparatus designed to impinge the fluid stream is connected to the sidewalls of the drip chamber. If the drip chamber is tilted or deformed for any reason such that the fluid strikes the apparatus at an angle, the fluid will flow across the apparatus to the sidewall and then down the sidewall forming an invisible "sheet" of fluid.

Thus, in view of the prior art, there is a need in the industry for a drip chamber for use with intravenous administration sets that includes an apparatus of a simple design positioned within the drip chamber such that the fluid strikes the apparatus and accumulates into droplets that are visible through the sidewalls of the drip chamber by medical personnel.

SUMMARY OF THE INVENTION

The drip chamber of the present invention relates to a drip chamber that includes an impinging member that impinges the flow of fluid flowing through a drip chamber to cause the fluid to accumulate into droplets visible to medical personnel. The drip chamber of the present invention is of a simple design that includes a single impinging member that is connected to the upper end of the drip chamber. The impinging member may be made from various materials, including, without limitation, plastic or metal, and may be either attached or molded directly to the upper end of the drip chamber. The impinging member includes an extension portion that extends down from the upper end of the drip chamber in parallel to the fluid flow and a pedestal portion that extends from the extension portion into the path of the fluid flow. The fluid strikes the impinging member, accumulates into visible droplets and then falls into the fluid pool formed at the bottom of the drip chamber. The impinging member does not make contact nor is connected to the sidewalls of the drip chamber.

Under normal operation, the impinging member will not interfere with the visibility and calculation of the flow rate of the fluid by medical personnel when the flow rate is such that the fluid droplets are visible (i.e. a visible 60 drops/cc). As drops of fluid strike the impinging member, the drops accumulate and then fall off of the impinging member into the fluid pool. However, when the flow rate of the fluid is increased and the fluid forms a high velocity stream, the drip chamber of the present invention impinges the fluid stream to "break" the stream and cause the fluid flow to form visible droplets of fluid on the pedestal portion of the impinging member. These droplets accumulate and fall from the impinging member into the fluid pool and because they are visible they allow medical personnel to calculate the flow rate of the fluid to the patient.

There are various advantages to the use of the drip chamber of the present invention. Because the drip chamber of the present invention results in a visible drip of the intravenous fluid at various flow rates, it allows medical personnel to immediately visually confirm that an intravenous flow of fluid has been established. This is particularly critical in certain situations, i.e., as in the period immediately after an intravenous cannula or catheter has been inserted into the patient.

Another advantage of the drip chamber of the present invention is the prevention of "run away drip" in which an inappropriate or excessive amount of intravenous fluid is inadvertently administered to a patient. This may occur in the situation where a practitioner boluses a drug and then opens the intravenous administration set fully, but is distracted by other tasks and is unable to recognize or see the intravenous fluid flowing through the drip chamber because the fluid has formed an indiscernible fluid stream. Before the practitioner realizes that the fluid is being delivered at a high rate, the patient has already been delivered an excessive volume of the intravenous fluid. Although a solid stream of fluid can be discerned upon careful scrutiny, a fluid drip is more easily determined and recognized by the practitioner as the practitioner performs other critical tasks. Thus, the drip chamber of the present invention serves to assist medical personnel from infusing an excessive amount of intravenous fluid into a patient and such fluid restriction may be particularly important with respect to certain "at risk" patients such as pediatric, renal failure or cardiac failure patients.

A further advantage of the drip chamber of the present invention is that it functions to cause a visible drip of the fluid even in circumstances where the drip chamber is deformed or slightly tilted and does not permit the fluid to flow down the sidewalls of the drip chamber forming an invisible "sheet" of fluid.

A further advantage of the drip chamber of the present invention is that it has the desirable result of limiting the formation of air bubbles in the fluid pool that collects in the bottom end of the drip chamber.

A further advantage of the drip chamber of the present invention is the simplicity in the design of the impinging member such that the manufacturing costs of the drip chamber are not significantly increased.

Although the drip chamber of the present invention is particularly useful with respect to "mini-drip" intravenous administration sets, the drip chamber of the present invention can be easily incorporated and used with almost any intravenous administration sets known and used in the medical industry, including, without limitation, drip chambers that incorporate a photo-voltaic drop sensor. If desired, the impinging member of the drip chamber of the present invention may be enlarged for use with larger infusion volume sets (i.e. 15 gtt/cc) or pressurized intravenous administration sets.

These and other objects and advantages of the present invention will become apparent from the following detailed description, the accompanying drawings and the appended claims.

BRIEF DESCRIPTION OF THE DRAWINGS

For a further understanding of the features and advantages of the present invention, reference should be made to the following detailed description taken in conjunction with the accompanying drawings in which like parts are given like reference numerals and wherein.

DETAILED DESCRIPTION OF THE PREFERRED EMBODIMENT

Figure 1:
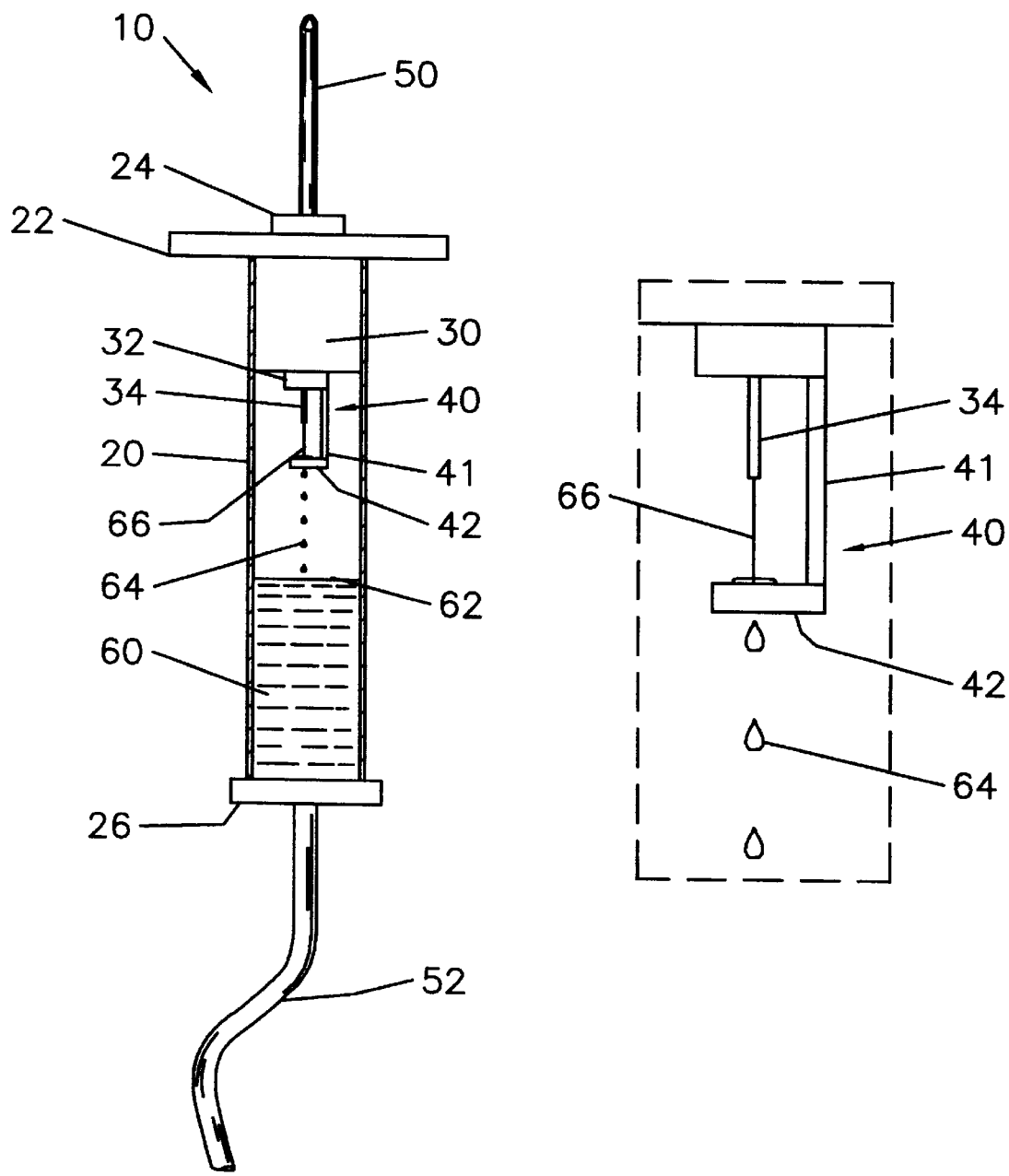
FIG. 1 is a front view of the drip chamber of the present invention showing an enlargement of the impinging member.
Figure 2:
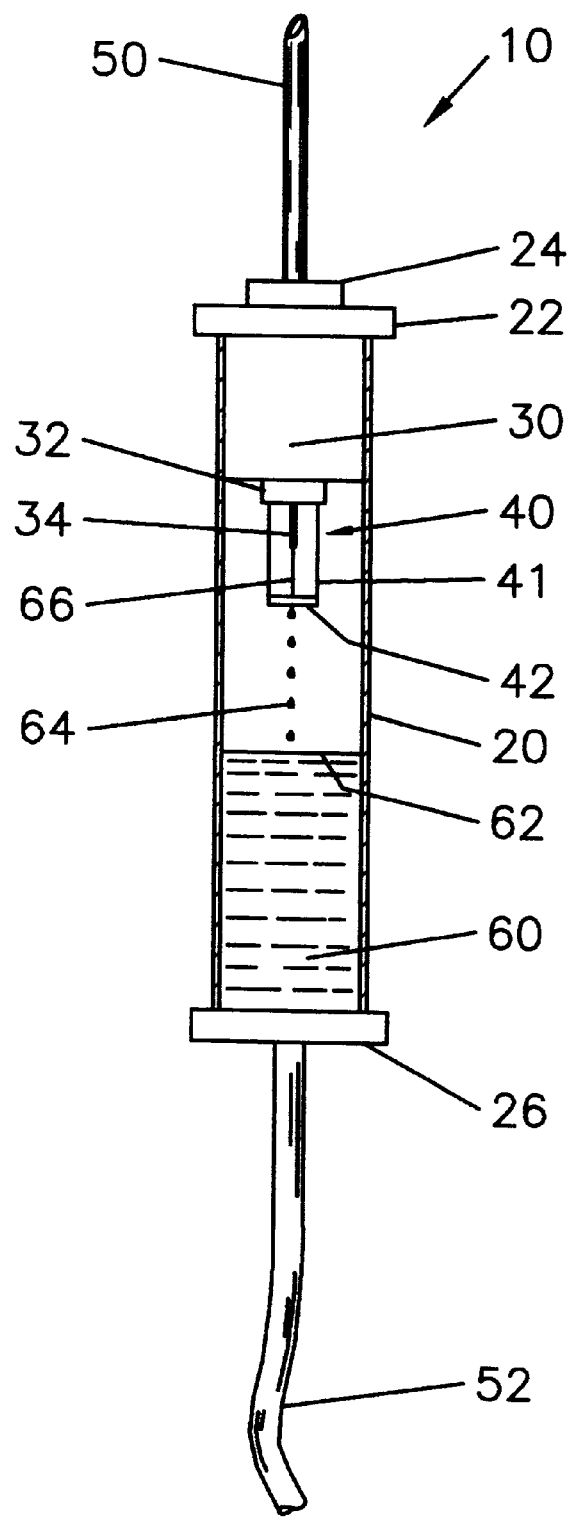
FIG. 2 is a side view of the drip chamber of the present invention.

Referring now to the drawings, FIGS. 1 and 2 illustrate the preferred embodiment of the apparatus of the present invention. As shown in FIG. 1, the drip chamber of the present invention is noted generally by reference numeral 10. The drip chamber 10 is designed to be placed in an intravenous flow path of an intravenous administration set as represented by input spike 50 and output tube 52. In a manner well known in the medical industry, the input spike 50 is connected to the fluid supply source and the output tube 52 is connected through the rest of the intravenous administration set to an intravenous needle for insertion into a medical patient.

As shown in FIGS. 1 and 2, the drip chamber 10 has a transparent cylindrical housing 20. The cylindrical housing 20 is preferably manufactured from a flexible plastic material to permit medical personnel to view the fluid within the drip chamber 10. The drip chamber 10 is provided with a top cap 22 connected to the upper end of the cylindrical housing 20 and a bottom cap 26 connected to the lower end of the cylindrical housing 20. Top cap 22 includes a shoulder 24 to brace the input spike 50 and to provide a sealed engagement with the input spike 50. The cylindrical housing 20 defines a reservoir portion 60 of the cylindrical housing 20 for collecting fluid in a fluid pool 62 within the drip chamber 10.

At its upper end, cylindrical housing 20 includes a sleeve member 30 integrally formed within the cylindrical housing 20. Sleeve member 30 includes a base 32 and a fine bore tube 34 mounted to the base 32 for support. Sleeve member 30 further includes a central bore aligned with input spike 50 and a fine bore tube 34 to communicate fluid from the input spike 50 to the fine bore tube 34. Attached to the base 32 and extending downward in spaced relation to the fine bore tube 34 is an impinging member noted generally be reference numeral 40. Impinging member 40 includes an extension portion 41 and a pedestal portion 42. Pedestal portion 42 extends from the extension portion 41 and is positioned under the fine bore tube 34 in order to impinge the fluid flowing from the fine bore tube 34. In the preferred embodiment, the pedestal portion 42 is a rectangular arm that extends perpendicularly from the extension portion 41, alternatively the pedestal portion 42, but may also be shaped as a spoon or disc.

In operation, fluid from input spike 50 flows through the central bore in top cap 22, sleeve member 30 and base 32 and into fine bore tube 34. If the flow rate of the fluid is at a level such that the fluid drops from the fine bore tube 34 in droplets, the droplets 64 will strike the pedestal portion 42 of the impinging member 40 and drop from the pedestal portion 42 into the fluid pool 62 in the reservoir portion 60 of the cylindrical housing 20. The flow rate of the fluid under such condition can be calculated by medical staff by observation of the fluid drip rate through the cylindrical housing 20. The impinging member 40 does not interfere with this calculation under these operating conditions.

When the flow rate of the fluid increases to the point that the fluid forms a fluid stream 66, the pedestal portion 42 of the impinging member 40 "breaks" the fluid stream 66 causing the fluid because of the fluid's cohesive forces to collect and form visible droplets 64. These visible droplets 64 then fall from the pedestal portion 42 of the impinging member 40. Because the fluid is in visible droplets 64 rather than a potentially indiscernible fluid stream 66, medical staff can calculate the flow rate of the fluid under such conditions by viewing the visible droplets 66 through the cylindrical housing 20 as they do under normal operating conditions. As the fluid drops from the impinging member 40, the fluid collects in the fluid pool 62 in the reservoir portion 60 of the cylindrical housing 20.

Although a preferred embodiment of the invention has been illustrated in the accompanying Drawings and described in the foregoing Detailed Description of the Preferred Embodiment, it will be understood that the invention is not limited to the embodiment disclosed but is capable of numerous modifications without departing from the scope of the invention as claimed.

What is claimed is:

1. A drip chamber for an intravenous fluid assembly comprising:

a transparent chamber housing having an inlet member and an outlet member formed to channel intravenous fluid flow through the transparent chamber housing; the inlet member including a sleeve member; the sleeve member having a base member and a fine bore tube mounted to the base member, the fine bore tube extending from the base member;

an impinging member attached to the base member and extending parallel to the fine bore tube such that the intravenous fluid flow is impinged when the intravenous fluid flow forms a fluid stream to cause the fluid to form visible fluid droplets.

2. The drip chamber of claim 1 wherein the impinging member includes a pedestal portion and an extension portion, the pedestal portion forming a rectangular arm that extends perpendicularly from the extension portion.

3. The drip chamber of claim 1 wherein the impinging member is substantially rigid.

4. The drip chamber of claim 1, wherein the transparent chamber housing is manufactured from a flexible plastic material.

* * * * *